United States Patent
Richter

(10) Patent No.: US 8,202,280 B2
(45) Date of Patent: Jun. 19, 2012

(54) DEVICE AND METHODS FOR NON-SURGICAL CLIPPING OF ANEURYSMS

(75) Inventor: Jacob Richter, Ramat Hasharon (IL)

(73) Assignee: Zuli Holdings Ltd., Tel Aviv (IL)

( * ) Notice: Subject to any disclaimer, the term of this patent is extended or adjusted under 35 U.S.C. 154(b) by 76 days.

(21) Appl. No.: 12/540,599

(22) Filed: Aug. 13, 2009

(65) Prior Publication Data
US 2009/0299383 A1 Dec. 3, 2009

Related U.S. Application Data

(62) Division of application No. 11/346,863, filed on Feb. 1, 2006, now Pat. No. 7,601,160.

(60) Provisional application No. 60/650,352, filed on Feb. 4, 2005.

(51) Int. Cl.
*A61B 17/10* (2006.01)
*A61M 29/00* (2006.01)

(52) U.S. Cl. ........................ 606/139; 606/200

(58) Field of Classification Search ............... 606/135, 606/136, 137, 139, 200; 623/1.11
See application file for complete search history.

(56) References Cited

U.S. PATENT DOCUMENTS

| | | | |
|---|---|---|---|
| 6,071,292 A | 6/2000 | Makower et al. | |
| 6,361,558 B1 * | 3/2002 | Hieshima et al. | 623/1.16 |
| 6,511,468 B1 | 1/2003 | Cragg et al. | |
| 6,666,882 B1 | 12/2003 | Bose et al. | |
| 2002/0022837 A1 | 2/2002 | Mazzocchi et al. | |
| 2004/0002718 A1 | 1/2004 | Trout et al. | |
| 2004/0210240 A1 | 10/2004 | Saint | |
| 2004/0260384 A1 | 12/2004 | Allen | |

FOREIGN PATENT DOCUMENTS

| | | |
|---|---|---|
| JP | 10-155800 A | 6/1998 |
| WO | WO 95/10983 | 4/1995 |
| WO | WO 02/39906 A2 | 5/2002 |
| WO | WO 2004/014435 A2 | 2/2004 |

OTHER PUBLICATIONS

International Search Report from corresponding application serial No. PCT/IB06/00178 mailed Aug. 1, 2008.
Extended European Search Report from corresponding European Application No. EP 06 727 243 (EP 1 855 600A) dated Jul. 10, 2009.
Office Actions and Responses to Office Actions of related pending U.S. Appl. No. 11/346,863: • Notice of Allowance dated Jul. 23, 2009; • Response to Election/Restriction Requirement dated Apr. 15, 2009; • Restriction/Election Requirement dated Mar. 19, 2009; • Amendment and Response to Non-Final Office Action dated Dec. 3, 2008; and • Non-Final Rejection dated Sep. 17, 2008.

* cited by examiner

*Primary Examiner* — Vy Q Bui
(74) *Attorney, Agent, or Firm* — Cadwalader Wickersham & Taft LLP

(57) ABSTRACT

The present invention relates to a device for the non-surgical clipping of aneurysms. The invention also includes methods of use to treat aneurysms, including intracranial aneurysms. The aneurysm is clipped by positioning a wire comprising a shape memory alloy, pre-set to a mutually twisted conformation, on opposite sides of the neck of the aneurysm and causing the wires to twist around each other. Thus, the aneurysm neck is substantially closed. The resulting thrombosis in the aneurysm further excludes the aneurysm from blood flow and pressure.

5 Claims, 4 Drawing Sheets

2

DEVICE AND METHODS FOR NON-SURGICAL CLIPPING OF ANEURYSMS

This application is a divisional of U.S. patent application Ser. No. 11/346,863, filed on Feb. 1, 2006, now U.S. Pat. No. 7,601,160, which claims the benefit of priority of U.S. Provisional Application Ser. No. 60/650,352, filed Feb. 4, 2005, the contents of which are incorporated by reference in toto.

FIELD OF THE INVENTION

The present invention relates to a device for the non-surgical clipping of aneurysms. The invention also encompasses methods of use to treat aneurysms, including intracranial aneurysms.

BACKGROUND OF THE INVENTION

An aneurysm is a phenomenon in which the wall of a blood vessel is abnormally dilated due to weakening of the vessel wall. Common areas where aneurysms occur and cause potential medical conditions include the cerebral arteries, coronary arteries, the carotid arteries, the thoracic aorta, and the abdominal aorta. Aneurysms pose a danger because the blood pressure within the aneurysm could cause the vessel to rupture. Vessel rupture, in turn, often causes dramatic negative health consequences, such as a stroke in the case of a cerebral vessel rupture.

In recent decades, the main surgical treatment of ruptured and unruptured intracranial aneurysms has been to expose the aneurysm in an open cranial procedure and to ligate the neck of the aneurysm using surgical clips ("clipping"). These open surgical procedures are associated with significant drawbacks. The surgical procedure is complex and requires experienced surgeons and well equipped surgical facilities. Even with the best surgeons and equipment, patients suffering from such aneurysms are often elderly and weakened from cardiovascular and other diseases. This factor reduces the number of patients eligible for surgery. Even for eligible patients prior to rupture, conventional aneurysm repair has a relatively high mortality rate, usually from 2 to 10%. Morbidity related to the conventional surgery includes myocardial infarction, renal failure, impotence, paralysis, and other conditions. Even with successful surgery, recovery takes several weeks and often requires a lengthy hospital stay. The location of an aneurysm may in many cases be buried in the brain and inaccessible from the outside and thus present no surgical option. In such cases, the aneurysm may only be accessible endovascularly.

Recently, many types of aneurysms have been treated endovascularly. Such techniques typically involve attempting to form a mass within the sac of the aneurysm. Typically, a microcatheter is used to access the aneurysm. The distal tip of the microcatheter is placed within the sac of the aneurysm, and the microcatheter is used to inject embolic material into the sac of the aneurysm. The embolic material includes, for example, detachable coils (e.g., Guglielmi Detachable Coils) or an embolic agent, such as a liquid polymer. The injection of these types of embolic materials suffer from disadvantages, most of which are associated with migration of the embolic material out of the aneurysm into the parent artery. This can cause permanent and irreversible occlusion of the parent artery. Additionally, over-packing the aneurysm is another potential disadvantage which could generate undesirable pressure in the aneurysm. Of particular concern are aneurysms having a wide connection to the blood vessel (e.g., wide neck aneurysms). Wide neck aneurysms have the additional risk that the occluded material will break free of the aneurysm and enter the parent blood vessel. Although treatment of an aneurysm by Detachable Coils is oftentimes long and involves many coils, the result is unpredictable and may not be successful at excluding blood flow from the aneurysm.

There remains, therefore, a need for a device and method for therapeutically treating aneurysms that has the accessibility of endovascular procedures combined with the efficacy of an open procedure without the associated risks.

SUMMARY OF THE INVENTION

The present invention relates to a device for the non-surgical clipping of aneurysms in a patient in need thereof. The device of the present invention comprises a guiding catheter encompassing a guiding needle. The guiding needle is a hollow tube with a needle tip at its distal end. A wire comprising a shape memory alloy is encompassed by the guiding needle and the guiding catheter. The diameters of each member are of a size such that each of the members can easily slide through the member that encompasses it.

Methods of using the device of the invention to treat aneurysms are also included in the present invention. In such methods, the aneurysm is clipped by positioning a wire comprising a shape memory alloy on each side of the neck of the aneurysm (using the guiding catheter and guiding needle) and causing the wires to twist around each other in the memorized shape, i.e., that had been set by a high heat treatment, for example. Thus, the aneurysm is substantially isolated from the lumen of the vessel and has a substantial reduction in blood flow and pressure. The reduced blood flow and pressure may cause thrombosis of the aneurysm and therefore reduces the risk of aneurysm rupture.

Any aneurysm can be treated according to the methods of the invention. In one specific embodiment, the aneurysm is an intracranial aneurysm.

DETAILED DESCRIPTION OF THE INVENTION

Figure 1:
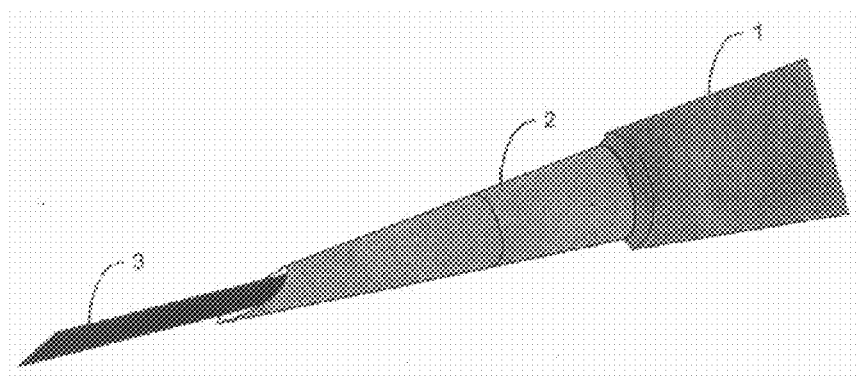
FIG. 1 is a schematic view of a guiding catheter 1 encompassing a guiding needle 2 which in turn encompasses a wire comprising a shape memory alloy 3. The guiding needle 2 has a sharp tip on its distal end.

FIG. 1 illustrates a device for the use in the non-surgical clipping of an aneurysm. The guiding catheter 1 encompasses a guiding needle 2 which encompasses a wire comprising a shape memory alloy 3.

The guiding catheter 1 is essentially any catheter known in the art capable of getting to the affected area (i.e., the lumen of a blood vessel or artery proximal to an aneurysm) and allowing the passage of a guiding needle.

The guiding needle 2 is a hollow tube with a needle tip at its distal end. The guiding needle can perforate the wall of the blood vessel thus allowing the properly shaped guiding needle to exit and re-enter the vessel lumen. The guiding needle can be made of any known material that can pass through the guiding catheter, and is shaped with the appropriate curvature such that it can exit and re-enter the vessel lumen, and that can deliver the wire comprising a shape memory alloy. Such materials include, but are not limited to, metal or a reinforced polymer material.

The wire comprising a shape memory alloy 3 is made from such metal alloy that allows it to be straight during deployment and then assume a pre-set twisted form that was thermo-mechanically predetermined, this transformation being triggered by a temperature step. The temperature step may be effected by changing the temperature of the environment around the wire, e.g., by hot fluid or body heat, or by passing current through the wire generating resistive heat.

Any shape memory alloy can be used to make the wire comprising a shape memory alloy. In specific embodiments, the shape memory alloy used is NiTi (e.g., NiTinol), CuZnAl, CuAlNi, or a mixture thereof (see, e.g., *Shape Memory Materials*, edited by Otsuka and Wayman, Cambridge University Press; October 1999 and *Shape Memory Alloys*, edited by Youyi and Otsuka, International Academic Publishers, June 1998).

Figure 2:
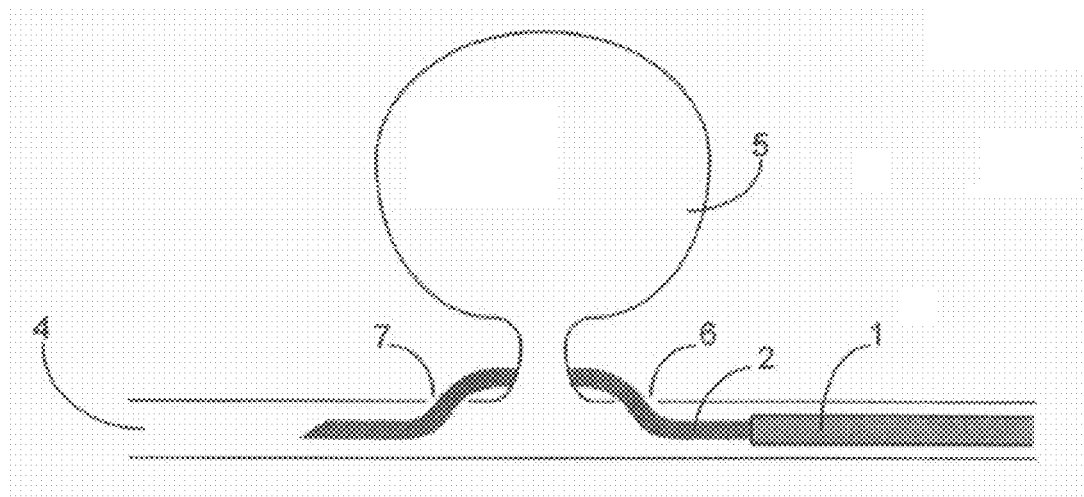
FIG. 2 is a schematic view of a cross section of a blood vessel with a lumen 4 and an aneurysm 5. The guiding catheter 1 is positioned in the lumen 4 proximal to the aneurysm 5. The guiding needle 2 is shown leaving the vessel lumen 4 through a first perforation 6 in the vessel wall immediately proximal to the aneurysm 5, tracking along a first side of the aneurysm 5, and re-entering the vessel lumen 4 through a second perforation 7 in the vessel wall distal to the aneurysm 5.

FIG. 2 illustrates the device whose tip is shown in FIG. 1. The device is positioned in the lumen 4 of a blood vessel proximal to an aneurysm 5. The guiding catheter can be passed through the body lumen to the affected area by any method known in the art. The affected area is identified by diagnostic methods known in the art, e.g., MRI, Angiogram, or the like. The location of the catheter can be monitored by any method known in the art. In one embodiment, the progress of the catheter through the lumen is monitored by a device that detects radiopacity of the catheter device such as angiographic equipment in X-ray. Increased radiopacity can be provided to the catheter by manufacturing (all or a part of) or coating (all or a part of) the catheter with one or more radiopaque materials.

The method of using the device to treat an aneurysm begins with the guiding needle 2 being deployed from the guiding catheter 1. The guiding needle 2 perforates the vessel wall (first perforation 6). The guiding needle is then passed through the first perforation 6 and leaves the vessel lumen 4 immediately proximal to the aneurysm 5. The guiding needle is then tracked along the exterior vessel wall until it passes the aneurysm 5 on a first side of the aneurysm. The guiding needle 2 perforates the vessel wall (second perforation 7) and passes through the perforation to re-enter the vessel lumen 4 immediately distal to the aneurysm 5. The position of the guiding needle can be monitored by any method known in the art. In one embodiment, the guiding needle is monitored by angiography. Increased radiopacity can be provided to the guiding needle by the means described supra.

Figure 3:
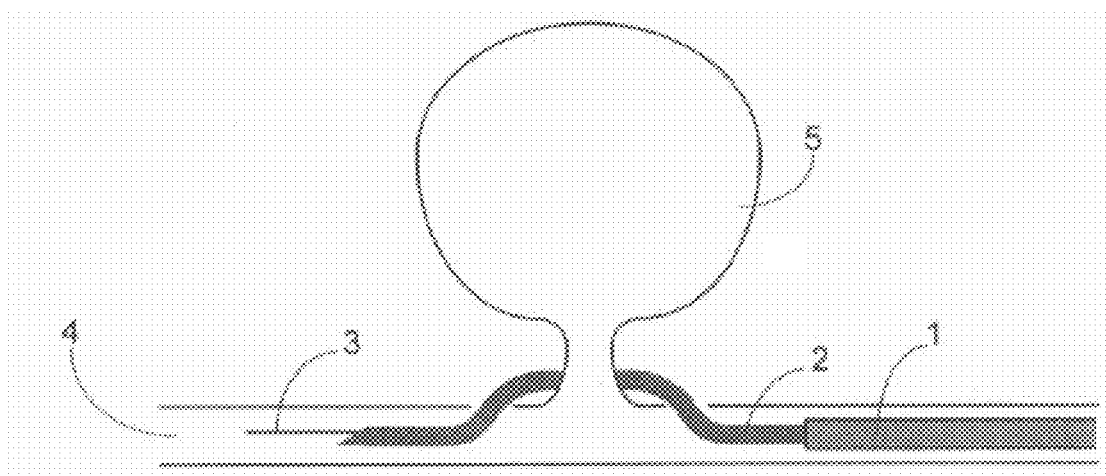
FIG. 3 is a view of a cross section of a blood vessel with a lumen 4 and an aneurysm 5. A first wire comprising a shape memory alloy 3 is shown being deployed from the guiding needle 2. The guiding catheter 1 remains positioned in the lumen 4 proximal to the aneurysm 5.

FIG. 3 illustrates the next step in the method of the invention to treat an aneurysm. A first wire comprising a shape memory alloy 3 is fed through and deployed from the guiding needle 2.

Figure 4:
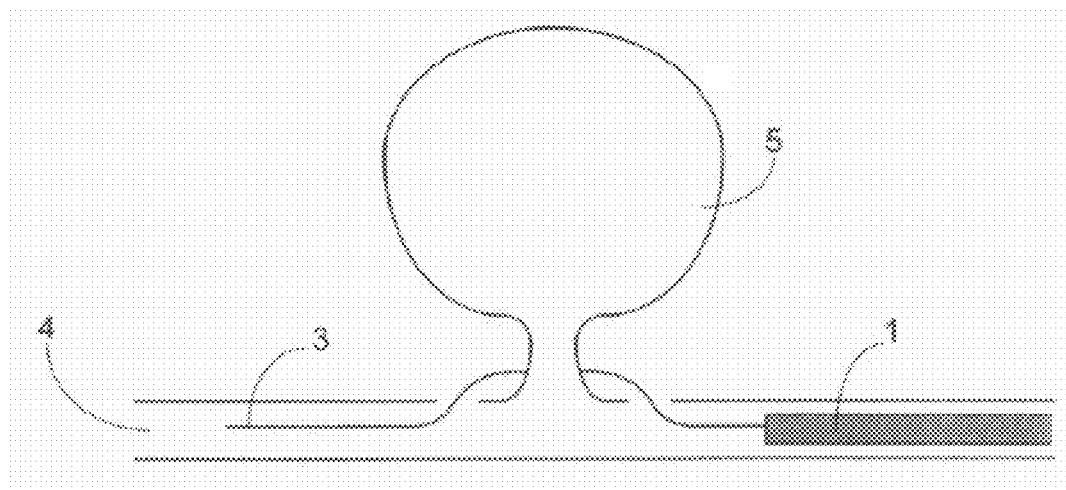
FIG. 4 is a view of a cross section of a blood vessel with a lumen 4 and an aneurysm 5. The guiding needle has been retracted back into the guiding catheter 1 though the first 6 and second 7 perforations leaving the first wire comprising a shape memory alloy 3 positioned around the first side of the aneurysm 5.

FIG. 4 illustrates the next step in the method of the invention to treat an aneurysm. The guiding needle is retracted back into the guiding catheter 1 though the first 6 and second 7 perforations leaving the first wire comprising a shape memory alloy 3 positioned around the first side of the aneurysm 5.

Figure 5:
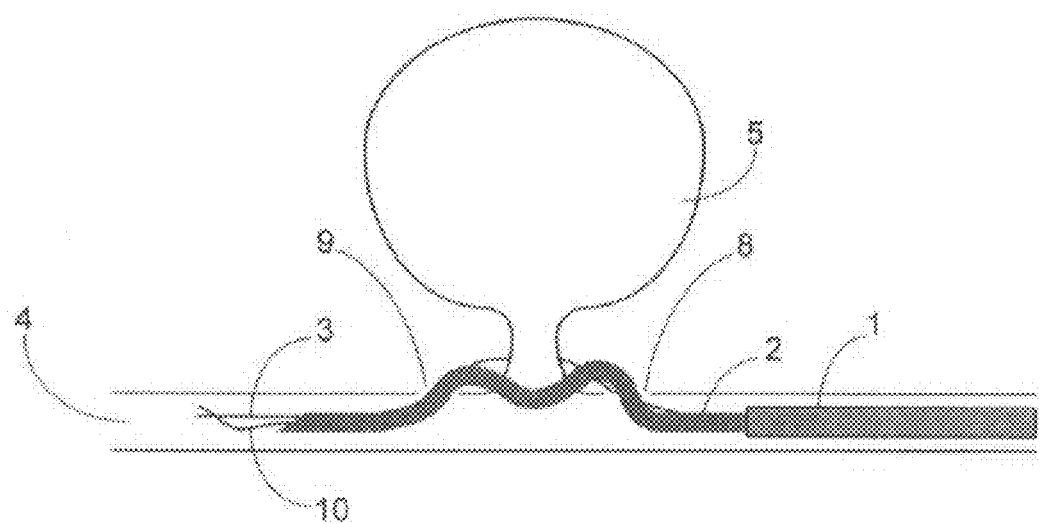
FIG. 5 is a view of a cross section of a blood vessel with a lumen 4 and an aneurysm 5. The guiding needle 2 is shown leaving the vessel lumen 4 through a third perforation 8 in the vessel wall immediately proximal to the aneurysm 5, tracking along a second side of the aneurysm 5, and re-entering the vessel lumen 4 through a fourth perforation 9 in the vessel wall distal to the aneurysm 5. A second wire comprising a shape memory alloy 10 is shown being deployed from the guiding needle 2. The guiding catheter 1 remains positioned in the lumen 4 proximal to the aneurysm 5. The first wire comprising a shape memory alloy 3 remains positioned around the first side of the aneurysm 5.

FIG. 5 illustrates the next step in the method of the invention to treat an aneurysm. The guiding needle 2 is deployed from the guiding catheter 1 for a second time. The guiding needle 2 perforates the vessel wall (third perforation 8). The guiding needle is then passed through the third perforation 8 and leaves the vessel lumen 4 immediately proximal to the aneurysm 5. The guiding needle is then tracked along the exterior vessel wall until it passes the aneurysm 5 on a second side of the aneurysm (the side of the aneurysm opposite the first wire comprising a shape memory alloy). The guiding needle 2 perforates the vessel wall (fourth perforation 9) and passes through the perforation to re-enter the vessel lumen 4 immediately distal to the aneurysm 5. A second wire comprising a shape memory alloy 10 is fed through and deployed from the guiding needle 2. Perforations 1 and 3 may be separate perforations or they may overlap. Perforations 2 and 4 may be separate perforations or they may overlap.

Figure 6:
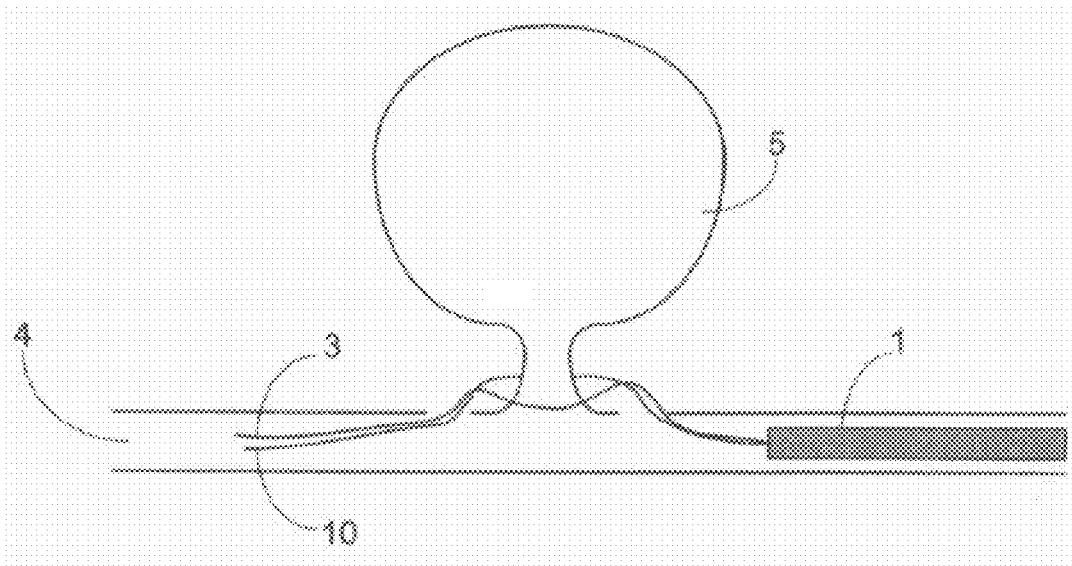
FIG. 6 is a view of a cross section of a blood vessel with a lumen 4 and an aneurysm 5. The guiding needle has been retracted back into the guiding catheter 1 though the third 8 and fourth 9 perforations leaving the second wire comprising a shape memory alloy 10 positioned around the second side of the aneurysm 5. The first wire 3 and the second wire 10 are on either side of the neck of the aneurysm 5.

FIG. 6 illustrates the next step in the method of the invention to treat an aneurysm. The guiding needle is retracted back into the guiding catheter 1 through the third 8 and fourth 9 perforations leaving the second wire comprising a shape memory alloy 10 positioned around the second side of the aneurysm 5 (i.e., opposite that of the first wire). The first wire 3 and the second wire 10 are now on either side of the neck of the aneurysm 5.

The first and second wires comprising a shape memory alloy have been pre-conditioned such that when heated they will revert to a mutually twisted configuration. This is accomplished by the first and second wires twisting around each other after heating them due to the pre-set twisted shape of the wires.

Figure 7:
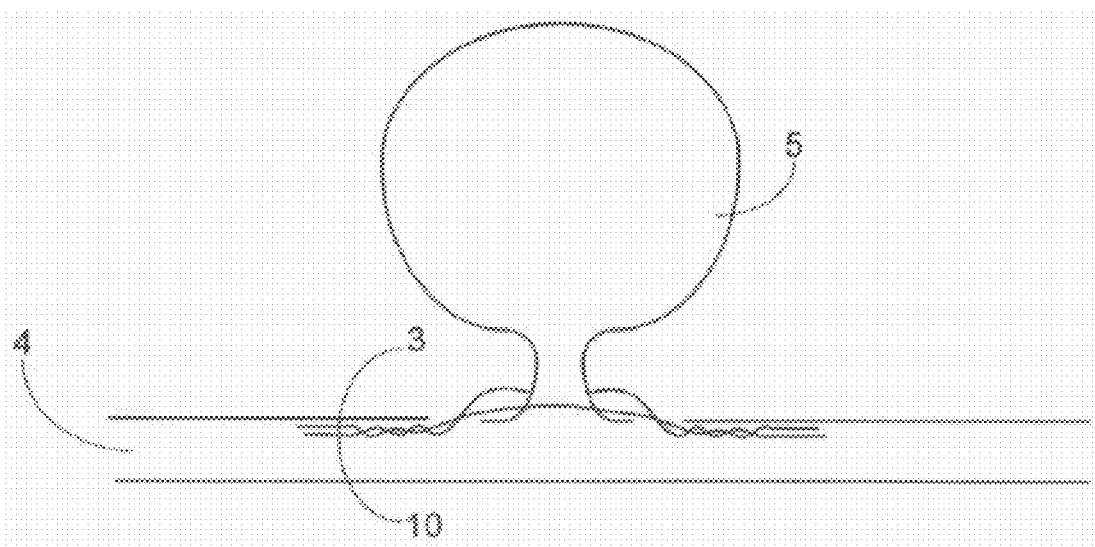
FIG. 7 is a view of a cross section of a blood vessel with a lumen 4 and an aneurysm 5. The first wire 3 and second wire 10 are twisted around each other. The neck of the aneurysm 5 has been substantially clipped.

FIG. 7 illustrates the last step in the method of the invention to treat an aneurysm. The guiding catheter and the guiding needle are retracted through the vessel and removed from the patient leaving the twisted first 3 and second 10 wires. The first wire 3 and second wire 10 are twisted around each other by application of moderate heat. Thus the neck of the aneurysm is pressed closed by the twisted wires.

The amount of heat necessary to cause the shape reversion of the wires will vary depending on, e.g., the type of shape memory alloy used, the thickness of the wire, etc. In one embodiment, the heat necessary to cause shape reversion is body heat. In another embodiment, the heat necessary to cause shape reversion is higher than body heat. In such embodiments, any means of applying the moderate heat necessary to cause the shape reversion of the first and second wires can be used. In a specific embodiment, a mild electric current may be passed through the wires to heat them. In another specific embodiment, there is heating by a hot fluid in the region of the wires.

By twisting wires 3 and 10, the neck of the aneurysm 5 has been substantially clipped by twisted wires 3, 10 and thus the blood flow from the lumen 4 of the vessel is reduced. This can be measured by methods known in the art. The reduction in blood flow would lead to thrombosis in the aneurysm and its further exclusion from blood circulation.

As various changes can be made in the above-described subject matter without departing from the scope and spirit of the present invention, it is intended that all subject matter contained in the above description, or defined in the appended claims, be interpreted as descriptive and illustrative of the present invention. Modifications and variations of the present invention are possible in light of the above teachings.

What is claimed is:

1. A device for treating a blood vessel aneurysm, said aneurysm being connected to said vessel by a neck, consisting essentially of: two shape memory alloy wires, each of said wires having been thermo-mechanically pre-set to a memorized twisted configuration, and a guiding needle configured to receive at least one of said wires, said guiding needle having a sharp tip for perforating a blood vessel wall; wherein said two wires have a generally straight, non-twisted deployment configuration and revert to said memorized twisted configuration when heated, wherein when deployed on opposite sides of said neck of said aneurysm and heated said two wires adopt a mutually twisted configuration, thereby pressing said neck of said aneurysm substantially closed to reduce pressure and blood flow into said aneurysm.

2. The device of claim 1, wherein said wires being a first wire and a second wire, the device further comprising:
    a guiding catheter.

3. The device of claim 1 or 2, wherein said shape memory alloy is NiTinol.

4. The device of claim 1 or 2, wherein said aneurysm is an intracranial aneurysm.

5. The device of claim 2, wherein said guiding catheter is adapted to deploy said guiding needle in a blood vessel; and wherein said guiding needle is configured to guide said first wire through said blood vessel wall to be deployed at a first side of said aneurysm and configured to guide said second wire through said blood vessel wall to be deployed at a second side of said aneurysm, wherein said second side is opposite said first side of the aneurysm.

* * * * *